United States Patent [19]

Naito et al.

[11] 4,146,710

[45] Mar. 27, 1979

[54] SOLID CEPHALOSPORIN SALT

[75] Inventors: Kenzo Naito, Kyoto; Kazuo Tsukamura, Hyogo; Haruo Sinbo, Kawanishi, all of Japan

[73] Assignee: Takeda Chemical Industries, Ltd., Japan

[21] Appl. No.: 828,842

[22] Filed: Aug. 29, 1977

[30] Foreign Application Priority Data

Aug. 31, 1976 [JP] Japan .................. 51-104583

[51] Int. Cl.² ........................................ C07D 501/36
[52] U.S. Cl. ..................................... 544/27; 424/246
[58] Field of Search ................................. 544/26, 27

[56] References Cited

U.S. PATENT DOCUMENTS 4,008,246  2/1977  Ochiai et al. ............................ 544/27
4,080,498  3/1978  Numaza et al. ......................... 544/27

Primary Examiner—Nicholas S. Rizzo

Attorney, Agent, or Firm—Wenderoth, Lind & Ponack

[57] ABSTRACT

A solid cephalosporin derivative having the formula:

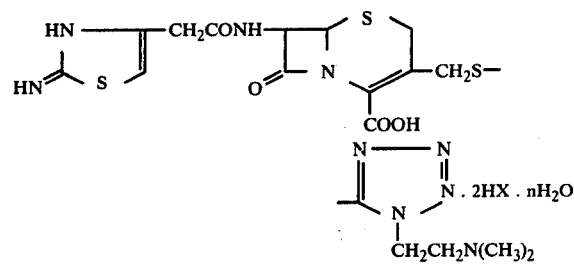

wherein X is chlorine or bromine, n is a number from zero to 6, is found to have high stability in storage and may be used as an active component of an antimicrobial composition.

4 Claims, No Drawings

SOLID CEPHALOSPORIN SALT

This invention relates to solid cephalosporin derivative of the formula:

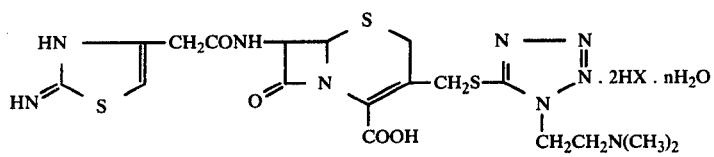

(wherein X is chlorine or bromine; n is a number from zero to 6) and a method of producing said derivatives.

Heretofore it is known that the compound having the formula:

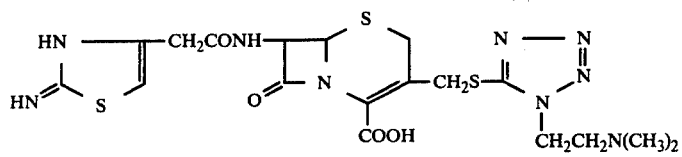

has an excellent antibiotic activity (West German Patent Application Laid Open No. 2461478). One of the disadvantages of compound (II) is that its purification is very difficult because of the presence of two basic groups, i.e. iminothiazoline and dimethylamino, and one carboxylic group within it molecule and its high water solubility. Another disadvantage is in its inadequacy in a long shelf-life because of being unstable in the free acid form (zwitter ion) or its salt with a base. The research undertaken to overcome these disadvantages has shown that a solid cephalosporin derivative (I) may be produced by reacting said compound (II) or a salt thereof with at least 2 molecular equivalents of an acid of the formula HX (where the symbol has the same meaning as defined hereinbefore), in the presence of water if necessary, and collecting the resulting solid materials; that the compound (I) thus obtained is highly stable in storage and, that where said compound (I) may be recovered in crystalline form, the impurities which are otherwise difficult to remove by conventional purification procedures can be almost completely removed. This invention is predicated on the above findings.

The compound of formula (I) includes no more than 6 molecules of water. There are six different hydrates, from mono- to hexahydrates, there also being cases in which less than one molecule of water is absorbed or/and incorporated, dependent upon the conditions of production, and even in such cases the compound may be recovered and isolated as crystals. While the anhydrates are amorphous or crystalline powders, they may carry less than one mole of absorbed or/and incorporated water. Normally, the compound (I) of which Water content determined by Karl Fischer's method is more than about 1%, shows crystalline form in powder X-ray diffraction pattern, and the compound of formula (I) of which Water content is more than about 0.3%, shows crystalline form under polarizing microscopic observation. The compound (I) can also be isolated as amorphous state in powder X-ray diffraction pattern and under polarizing microscopic observation. These products also invariably fall within the scope of this invention. In terms of stability and purity, n is preferably in the range of $0.1 \leq n \leq 4$, and especially preferably in the range of $1 \leq n \leq 2$ in which case the compound (I) is in the form of crystal. From a commercial point of view, such products are desirable as having n value about 1 or about 2. The compound (I) also may contain a small quantity of reaction solvent such as methanol, ethanol, propanol or acetone, and these solvent-incorporated-compounds are also involved in the compound (I) of the present inventions.

The compound (I) may be prepared by per se known means. That is to say, the compound (I) may be obtained, e.g. by reacting the starting material compound (II) or a salt thereof with at least 2 molecular equivalents of an acid of the formula HX, in the presence of water if necessary, and collecting the resulting solid materials. As the starting compound (II), use may be made, for example, of (1) the reaction mixture in which the compound (II) has been synthesized, (2) solution obtained by removing most part of impurities from this reaction mixture, (3) powder obtained by admixture of the solution obtained in (2) with a solvent in which the compound (II) is only sparingly soluble, and (4) powder obtained by concentrating to dryness or lyophilizing the solution obtained in (2). The starting compound (II) may be subjected to the present reaction in the free form (zwitter ion), or in the form of a salt with an alkali metal or alkaline earth metal such as sodium, potassium, lithium, or organic amine such as triethylamine, di-n-butylamine or di-cyclohexylamine. The acid HX is hydrochloric acid or hydrobromic acid, and may be one obtainable as a by-product in preparing the starting material (II). The acid is used in amounts normally within the range of 2 to 10 molecular equivalents and preferably within the range of 2 to 6 equivalents, any amount less than 2 moles per mole of starting compound (II) resulting in some difficulty to obtain homogeneous crystals while an unproportionally large excess of the acid could cause a decomposition of starting compound (II). In consideration of operational facility, yield, purification efficiency, etc., the reaction is normally carried out in the presence of water or an organic solvent, or a mixture thereof. The organic solvent for use in the reaction may be (1) a solvent in which the contemplated compound (I) is only sparingly soluble and which is soluble in water, e.g. ethanol, n-propanol, isopropanol, butanol, isobutanol, acetone, methyl ethyl ketone, acetonitrile, tetrahydrofuran, dioxane or the like (2) a mixture of a solvent such as those mentioned above (1) and a solvent in which the contemplated compound (I) is readily soluble and which is soluble in water, e.g. methanol, dimethylsulfoxide, formamide, N,N-dimethylformamide, N,N-dimethylacetamide, methylcellosolve or the like, or (3) a mixture of such a solvent as above (1) or mixture as above (2) with a solvent in which the contemplated compound (I) is only sparingly soluble and which is difficulty soluble in water, e.g. ethyl acetate, ether, dichloromethane, chloroform or the like. Particularly desirable are mixtures of water with acetone, ethanol, n-propanol, isopropanol, methyl ethyl ketone, tetrahydrofuran, etc. The reaction is normally conducted at a temperature in the range of −10° to +40° C., preferably 0° to +30° C. Below −10° C., the crystals are slow to grow, while any temperature over 40° C. is disadvantageous in that the starting compound (II) is decomposed. The reaction time depends upon the purity of starting compound (II) and the type of impurity contained but, when use is made of material (II) having a purity of more than 80 percent as obtained by a conventional purification procedure such as chromatography on an adsorbant column, the reaction is conducted for 30 minutes to 24 hours, preferably 30 minutes to 4 hours. The reaction product is isolated by filtration, centrifugation or lyophilization, for instance. When the organic solvent is included in the isolated compound (I), the compound (I) may be used as it is if the included organic solvent does not harm its stability in storage and its usage.

The following are preferred modes of embodiment of this invention.

(A) The compound (II) is dissolved in such a solvent as mentioned above, followed by the addition of a calculated amount of HX (wherein X is as hereinbefore defined). The reaction product is lyophilized. The lyophilizate is dried under reduced pressure and in the presence of a dehydrating agent such as silica gel, phosphoric anhydride or the like, thereby to obtain the anhydrate of compound (I).

(B) The compound (II) or its salt is dissolved in water or a mixture of water with one of the aforementioned hydrophilic organic solvents, followed by the addition of HX. After the reaction has been completed, an organic solvent in which said contemplated compound (I) is only sparingly soluble is gradually added to the resultant solution until the solution begins to take on turbidity. The solution is allowed to stand for 1 to several hours, then an organic solvent in which the contemplated compound (I) is only sparingly soluble is gradually added until crystals cease to separate out. The crystals thus obtained are recovered by a procedure such as filtration or centrifugation. The crystals take various forms of hydrates depending on the crystallization conditions, e.g. temperature, solvent or crystallization time, but are normally tri- to deca-hydrates. The crystals obtained sometimes carry small amounts of an organic solvent depending on the reaction conditions, but such organic solvent usually can be removed by drying under reduced pressure, if necessary. However, some kinds of organic solvents are difficult to remove by simply drying under reduced pressure and in this case, the crystals are desirably contacted with water vapor until about 5 to 10 molecular equivalents of water per mole of the anhydrate of compound (I) has been absorbed, thereby the organic solvent is removed. The obtained water-containing product is then held under reduced pressure (about 0 to 20 mmHg), whereby the water is gradually removed to yield crystals of the hexahydrate, pentahydrate, tetrahydrate and then trihydrate in the order mentioned. As the trihydrate crystals are allowed to stand under reduced pressure as above and in the presence of a dehydrating agent such as phosphoric anhydride, there are obtained crystals of the dihydrate, monohydrate and finally anhydrate in the order mentioned. Less than one mole of water may be contained (absorbed or incorporated) in these crystals. Alternatively, less than one mole of water as removed from the various hydrates may be considered to be contained (absorbed or incorporated) in these hydrates and there may be obtained a mixture of dissimilar hydrates.

(C) The above lyophilizate (A) is contacted with water vapor, whereupon the vapor is absorbed to yield crystals of hydrate. As the crystals are dried, the hexahydrate, pentahydrate, tetrahydrate, trihydrate, dihydrate, monohydrate and anhydrate are obtained in the order mentioned, with less than one mole of water being contained (absorbed or incorporated) in these hydrates and anhydrate.

(D) The compound (II) or its salt is dissolved in water containing about 5 to 35% of MX (wherein M means sodium, potassium and lithium, X means chlorine or bromine), followed by the addition of HX. By cooling of the solution the contemplated compound (I) begins to precipitate as crystals. The crystals thus obtained are recovered by a procedure such as filtration or centrifugation. As the crystals are dried, the pentahydrate, tetrahydrate, trihydrate, dihydrate, monohydrate and anhydrate are obtained in the order mentioned, with less than one mole of water being contained (absorbed or incorporated) in there hydrates and anhydrate.

(E) To the mixture of compound (II) or its salt and the aforementioned organic solvent in which the contemplated compound (I) is soluble is added anhydrous HX. The resulting mixture is filtered, if necessary, and the filtrate is mixed with the aforementioned organic solvent in which the contemplated compound (I) is sparingly soluble. The resulting precipitates recovered by a procedure such as filtration or centrifugation are dried under reduced pressure and in the presence of a dehydrating agent such as silica gel, phosphoric anhydride or the like, thereby amorphous powder of the anhydrate of compound (I) is obtained. The resultant crystals of contemplated compound (I) contain 2 moles of HX per mole of starting compound (II) as confirmed by elemental analysis and titration or other quantiative analysis. The crystallinity of the compound (I) may be established by microscopic observation, polarizing microscopy or X-ray diffraction analysis. The infrared absorption spectrum of the product shows narrow sharp peaks unlike those associated with the non-crystalline powders. There are cases in which the evidence of crystallinity disappears from the powder X-ray diffraction pattern when the water content of the contemplated crystals has been reduced to less than one mole by drying, but interference colors (signs of crystallinity) are still observed under a polarizing microscope.

The products obtained by the above modes (A) and (E) are usually amorphous in a powder X-ray diffraction pattern and under polarizing microscopic observation and are inferior in stability and purity to the products obtained by the above modes (B), (C) and (D), while, among the products, there are some which have then lost the cristallinity due to loss of crystal water (generally less than 0.3%).

The contemplated compound (I) according to this invention may be put to use in the form of crystals or/and as the non-crystalline powder obtainable by drying such crystals, or in some case as amorphous powder, or may be used as injectable or oral preparations in conjunction with a nontoxic alkali or alkaline earth metal salt, e.g. sodium hydrogen carbonate, sodium carbonate or trisodium phosphate, that is to say, after adjustment to the desired pH, ionic type and ionic strength. For example, a solution of contemplated compound (I) in an aqueous solution containing a stoichiometrically equivalent amount of sodium carbonate (hereinafter called the 'C' solution) may not only be employed as a local germicide, e.g. a disinfectant for surgical instruments, hospital rooms, drinking water, etc., but also be intramuscularly or intravenously administered to warm-blooded animals including man, mouse, rat and dog for the treatment of infectious diseases as caused by Gram-positive bacteria (e.g. *Staphylococcus aureus*) or Gram-negative bacteria (e.g. *Escherichia coli, Klebsiella pneumoniae, Proteus vulgaris, Proteus morganii*, etc.). When the contemplated compound (I) is used as a local disinfectant for surgical instruments, an aqueous solution containing 100 γ (on anhydrate basis) of compound (I) per milliliter may be prepared and sprayed over the instruments. For the management of a urinary tract infection caused by *Escherichia coli* in man or mouse, the "C" solution containing about 5 to 50 mg (on anhydrate basis) of contemplated compound (I) per kilogram body weight may be intravenously administered daily in three divided doses.

REFERENCE EXAMPLE

The antibacterial potency (in terms of MIC) and toxicity of the contemplated compound (I) on anhydrate basis

| (1) Antibacterial spectrum (agar dilution) | |
|---|---|
| *Staphylococcus aureus* FDA 209 P | 0.39 mcg/ml |
| *Staphylococcus aureus* 1840 | 0.78 mcg/ml |
| *Escherichia coli* NIHJ JC-2 | 0.2 mcg/ml |
| *Escherichia coli* O-111 | 0.05 mcg/ml |
| *Escherichia coli* T-7 | 1.56 mcg/ml |
| *Klebsiella pneumoniae* DT | 0.1 mcg/ml |
| *Proteus vulgaris* IFO 3988 | 1.56 mcg/ml |
| *Proteus morganii* IFO 3848 | 0.39 mcg/ml |

(2) Acute toxicity (mouse, intraperitoneal)

$CD_{50} \geqq 20 g/kg$

The acute toxicity data relates to a 1:1 (by mole) mixture of contemplated compound (I) and sodium carbonate.

It should be noted that the contemplated compound (I) of this invention may assume a tautomeric form on tautomerization as shown below.

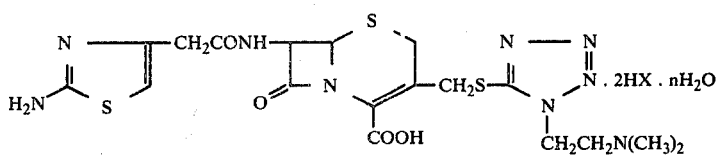

Many investigations have been made as to the modes of existence of this type of compound, the existing literature referring to the thiazoline form of the compound under certain circumstances [Acta Crystallographica 27, 326 (1971)] and the thiazole form in other circumstances [Chemistry and Industry, 1966 ed., P. 1634]. However, the results of various determinations suggest that the contemplated compound (I) according to this invention is stable in the thiazoline form by virtue of contribution of hydrogen bonding as shown by the following formula;

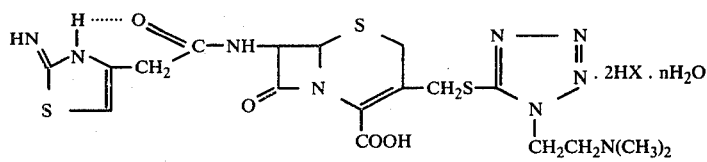

thus predominantly assuming this thiazoline form. However, it is possible that this equilibrium will shift to either side according to the circumstances in which the compund (I) occurs, for example the pH and polarity of the solvent, temperature and other parameters. Therefore, the contemplated compound (I) is referred to herein on the basis of its thiazoline form, although it may of course be otherwise designated according to the thiazole form.

The present invention is illustrated in further detail below with reference to examples, but it is to be understood that the examples are solely for the purpose of illustration and not to be construed as limitations of the invention, and that many variations may be resorted to without departing from the spirit and scope of the invention. In this specification, "g", "mm", "kg", "ml", "l", "cm", "ppm", "MHz", "M", "mcg", "Calcd.", "temp." and "min." are abbreviations of "gram", "millimeter", "kilogram", "milliliter", "liter", "centimeter", "part per million", "mega Herz", "Mole", "microgram", "Calculated", "temperature" and "minute", respectively. Resins named "Amberlite" are products manufactured by Rohm & Haas Co. in U.S.A. All the temperatures are uncorrected and the percentages are all on weight basis except specifically defined. The NMR spectra given therein were measured using a Varian Model HA 100 (100 MHz) or T60 (60 MHz) spectrometer with tetramethylsilane as the internal or external reference and all τ values are in ppm. The symbol s stands for a singlet, d a doublet, t a triplet, dd a double doublet and m a multiplet and sh a shoulder. Water Content in the following Examples are all determined by Karl Fischer's Method.

EXAMPLE 1

(1) To 400 g of 2-(N,N-dimethylamino)ethylamine was added 2.4 l of ether and, after cooling, a mixture of 400 g of carbon disulfide and 4.0 l of ether was added dropwise at 18°–23° C. over a period of 1 hour. The mixture was stirred further at a temperature of the same range for 1 hour and the resultant crystals of 2-(N,N-dimethylamino)ethylamine carbodithioic acid were recovered by filtration and dried. Yield 695 g.; % yield 93.3%; melting point: 156°–157° C.

To the above crystals was added 4.4 l of water and, under stirring at 8°–13° C., 4.32 l of 1N-KOH was added dropwise over a period of 30 to 40 minutes. Then, at 0°–5° C., a mixture of 668 g of methyl iodide and 6.68 l of acetone was added dropwise over 30–40 minutes, followed by 30 minutes' stirring at a temperature of the same range. The acetone was distilled off under reduced pressure and the aqueous layer was extracted with 3 l and 2 l portions of ethyl acetate. The ethyl acetate layers were pooled, washed with 2 l of a saturated aqueous solution of sodium chloride, dried over anhydrous sodium sulfate and concentrated. The crystalline residue was recrystallized by the addition of 500 ml of n-hexane. By the above procedure was obtained 575 g. of S-methyl-[2-(N,N-dimethylamino)]ethylamine carbodithioate. % yield 75.5%; melting point: 61°–62° C. To 520 g of the above crystals were added 1.05 l of ethanol, 190 g of sodium azide and 2.1 l of pure water, and the mixture was heated under reflux for 3 hours. To this was added a solution of 52 g of S-methyl-[2-(N,N-dimethylamino)-]ethylamine carbodithioate crystals in 100 ml of ethanol, followed by refluxing for 1 hour. The mixture was cooled to 20° C., and, following addition of 2.0 l of pure water, it was adjusted to pH 2 to 2.5 with concentrated hydrochloric acid in streams of nitrogen. The ethanol was distilled off under reduced pressure and the residue was passed over Amberlite IR-120 (H-form), the resin being thereafter washed with pure water until acidity has disappeared. The fractions eluted with 5% aqueous ammonia were pooled and concentrated. As crystals, 350 g of 1-[2-(N,N-dimethylamino)ethyl]-5-mercapto-1H-tetrazole was obtained. % yield 69.3%; melting point: 218°–219° C.

NMR(in $D_2O$, with a stoichiometric amount of $NaHCO_3$)τ:

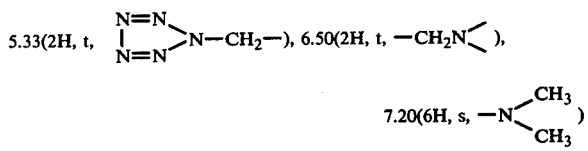

(2) To 2.6 l of water was added 206 g of 7β-[2-(2-imino-4-thiazolin-4-yl)acetamido]-3-acetyloxymethyl-3-cephem-4-carboxylic acid and, under stirring, 86.5 g of the 1-[2-(N,N-dimethylamino)ethyl]-5-mercapto-1H-tetrazole obtained in (1) above was added together with 42 g of sodium hydrogen carbonate. The mixture was stirred at 65° C. for 75 minutes, after which time it was cooled to 10° C. The mixture was adjusted to pH 2.0 by the addition of 250 ml of 5N-HCl and the resultant insolubles were collected by filtration and washed with water. The filtrate and washings were pooled, adjusted to pH 5.2 with sodium hydrogen carbonate and run onto a column of 10 l of Amberlite XAD-2 (100–200 mesh). The column was washed with 60 l of water, and elution was carried out with 20% methanol and, then, with 40% methanol. 11 liters of fractions containing the contemplated product are concentrated to 5 l and passed through a column of 300 g of activated aluminum oxide ["Activated Alumina" (about 300 mesh) manufactured by Wako Pure Chemical Industries, Ltd. in Japan] and a column of 100 ml of Amberlite IR-120(H-form). The column was washed with water. The effluent and washings were pooled and concentrated to 2 l. The concentrate was cooled to 5° C. and stirred with 5 g of activated charcoal for 5 minutes, then the charcoal was filtered off. The filtrate was lyophilized. By the above procedure was obtained 51.2 g of 7β-[2-(2-imino-4-thiazolin-4-yl)acetamido]-3-[1-(2-(N,N-dimethylamino)ethyl]-1H-tetrazol-5-yl]thiomethyl-3-cephem-4-carboxylic acid. NMR(60 MHz, $D_2O$) τ: 3.45 (s, thiazoline 5-H); 4.35(d, 7-H); 4.88(d, 6-H); 5.0–6.7(m, 5×$CH_2$); 6.95(s, 2×$CH_3$)

(3) In 1.0 l of water was dissolved 263 g of a lyophilizate of 7β-[2-(2-imino-4-thiazolin-4-yl)acetamido]-3-[1-[2-(N,N-dimethylamino)ethyl]-1H-tetrazol-5-yl]thiomethyl-3-cephem-4-carboxylic acid as obtained by repeating six times the procedure of (2) above, purity which determined by high-speed liquid chromatography was 93% on anhydrate basis, followed by the addition of 1.0 l of acetone and, then, 150 ml of 12N-HCl.

Following addition of 20 g of activated charcoal to this solution, the mixture was stirred at 5° C. for 10 minutes, and then the charcoal was filtered off. To the filtrate was added 5 l of acetone and the mixture was stirred at 10° C. for 1 hour. Then, 2 l of acetone was further added and, after an hour's stirring, the resultant crystals were collected by filtration, washed 4 times with 500 ml portions of acetone and dried. By the above procedure was obtained 262 g crystals of said carboxylic acid dihydrochloride monohydrate (yield 94% on its pure product basis).

IR(KBr)cm$^{-1}$: 1770(β-lactam)

Elemental analysis, for $C_{18}H_{23}N_9O_4S_3 \cdot 2HCl \cdot H_2O$:
Calcd.: C, 35.06; H, 4.47; N, 20.45; S, 15.60; Cl, 11.50;
Found: C, 34.87; H, 4.52; N, 20.01; S, 15.33; Cl, 11.24

Water Content: Calcd. 2.92%; Found 3.15%

NMR(60MHz, $D_2O$) Υ: 3.20(s, thiazoline 5-H), 4.25(d, 7-H), 4.75(d, 6-H), 4.9–6.5(m, 5×$CH_2$), 6.85(s, 2×$CH_3$)

The purity of this product as determined by high-speed liquid chromatography was 99.6% on anhydrate basis and the powder X-ray diffraction pattern of the product showed that it was crystalline.

Conditions of liquid chromatography:

Partition column: Hitachi Ion Exchange Resin 2614 (manufactured by Hitachi, Ltd., Tokyo Japan), 2.1 mm×50cm; column temp. 50° C.; eluant-0.3M citrate buffer, pH 6.5, 0.2ml/min.; pressure 4.3 kg/cm$^2$; recorder sensitivity 10 mV; recording paper speed 2.5 mm/min.

(4) In the presence of phosphoric anhydride and at 35° C., 10 g of the crystals obtained in (3) above were dried in vacuo (2 mmHg) for 3 hours to obtain 9.8 g powder of said carboxylic acid dihydrochloride 0.64 hydrate. Water Content: 1.9%.

Based on its powder X-ray diffraction pattern, this product was found to be non-crystalline powder. Observation with a polarizing microscope showed that rotation of the object stage caused the product to produce interference color through crossed Nicol prisms, attesting to optical anisotropy and therefrom crystalline powder.

(5) In 200 ml of water was dissolved 20 g of the crystalline product obtained in (3) and the solution was cooled to 10° C. The solution was passed through a column of 135 ml of Amberlite IR-45(OH-form) over a period of 30 minutes and the column was washed with 300 ml of water. The effluent was lyophilized to recover 16.0 g of 7β-[2-(2-imino-4-thiazolin-4-yl)acetamido]-3-[1-[2-(N,N-dimethylamino)ethyl]-1H-tetrazol-5-yl]thiomethyl-3-cephem-4-carboxylic acid. Water Content of this product was 3.20%, with its purity as determined by high-speed liquid chromatography being 99.2% on anhydrate basis.

EXAMPLE 2

In 30 ml of water was dissolved 10 g of 7β-[2-(2-imino-4-thiazolin-4-yl)acetamido]-3-[1-[2-(N,N-dimethylamino)ethyl]-1-H-tetrazol-5-yl]thiomethyl-3-cephem-4-carboxylic acid obtained in Example 1-(2) and, under stirring at 5° C., 5.5 ml of 12N-HCl and 150 ml of methyl ethyl ketone was added. The mixture was stirred for 3 hours and, then, allowed to stand at 5° C. overnight. The resultant crystals were collected by filtration, washed 4 times with 20 ml portions of methyl ethyl ketone and dried. By the above procedure was obtained 10.5 g crystals of said carboxylic acid dihydrochloride dihydrate.

Elemental analysis, for $C_{18}H_{23}N_9O_4S_3.2HCl.2H_2O$: Calcd.: C, 34.07; H, 4.61; N, 19.86; Cl, 11.17; Found: C, 33.94; H, 4.80; N, 20.02; Cl, 11.15

Water Content: Calcd. 5.68%; Found 5.80%

EXAMPLE 3

In 1.5 ml of water was dissolved 0.53 g of 7β-[2-(2-imino-4-thiazolin-4-yl)acetamido]-3-[1-[2-(N,N-dimethylamino)ethyl]-1H-tetrazol-5-yl]thiomethyl-3-cephem-4-carboxylic acid obtained in Example 1-(2) and, at 5° C., 0.7 ml of 5N-aqueous solution of HBr was added. Following the addition of 11 ml of acetone, the mixture was stirred at 10° C. for 2 hours. Then, 5 ml of acetone was further added and the mixture was stirred at 25° C. for 1 hour. The resultant crystals were collected by filtration, washed 5 times with 2 ml portions of acetone and dried in the air. The product was then dried in vacuo to obtain 0.56 g crystals of said carboxylic acid dihydrobromide dihydrate.

NMR(60 MHz, in $D_2O$) τ: 3.22(s, thiazoline 5-H), 4.26(d, 7-H), 4.75(d, 6-H), 4.9–6.5(m, 5×$CH_2$), 6.88(s, 2×$CH_3$).

The crystallinity of this product was confirmed by powder X-ray diffraction and polarizing microscopic observation.

EXAMPLE 4

(1) In 50 ml of water was dissolved 5.26 g of a lyophilizate of 7β-[2-(2-imino-4-thiazolin-4-yl)acetamido]-3-[1-[2-(N,N-dimethylamino)ethyl]-1H-tetrazol-5-yl]thiomethyl-3-cephem-4-carboxylic acid prepared in a similar manner as Example 1-(2), using 15 g for 5 g of activated charcoal (Water content of which was 3.2%, with its zwitter ion component as determined by high-speed liquid chromatography being 95.5%). The solution was cooled to 5° C. and 18.7 ml of 1N-HCl was added. Upon lyophilization, there was obtained 6.2 g of said carboxylic acid 2HCl.1.5$H_2O$ in powdery form.

Water Content: 4.2%(calcd. for $C_{18}H_{23}N_9O_4S_3.2HCl.1.5H_2O$: 4.3%)

Elemental analysis, for $C_{18}H_{23}N_9O_4S_3.2HCl.1.5H_2O$: Calcd.: C, 34.56; H, 4.19; N, 20.15; Cl, 11.33; Found: C, 34.21; H, 4.03; N, 19.82; Cl, 11.50

Purity as anhydrate (determined by high-speed liquid chromatography): 95.3%

Powder X-ray diffraction pattern: Non-crystalline.

Polarizing microscopy (crossed Nicol prisms): no interference colors were observed when the slide was rotated, attesting to non-crystalline powders.

(2) Two grams of the product obtained in (1) above were dried in vacuo in a silica gel desiccator to obtain 1.9 g of said carboxylic acid.2HCl.0.17$H_2O$ in powdery form.

Water Content: 0.5% (Calcd. for $C_{18}H_{23}N_9O_4S_3.2HCl.0.17H_2O$ : 0.5%); Purity as anhydrate (as determined by high-speed liquid chromatography): 95.3%; Powder X-ray diffraction pattern: non-crystalline; Polarizing microscopy: no interference colors.

(3) In 0.5 g of pure water was dissolved 1 g of a lyophilizate of the 7β-[2-(2-imino-4-thiazolin-4-yl)acetamido]-3-[1-[2-(N,N-dimethylamino)ethyl]-1H-tetrazol-5-yl]thiomethyl-3-cephem-4-carboxylic acid.2HCl.1.5$H_2O$ obtained in (1) above and the solution was allowed to stand at 5° C. for 15 hours. It was then dried in a phosphoric anhydride desiccator to obtain 1.05 g crystals of said carboxylic acid dihydrochloride dihydrate.

Elemental analysis, for $C_{18}H_{23}N_9O_4S_3.2HCl.2H_2O$: Calcd.: C, 34.07; H, 4.61; N, 19.86; S, 15.16; Cl, 11.17; Found: C, 33.84; H, 4.63; N, 19.71; S, 15.40; Cl, 11.29

Water Content: 6.00% (calcd. 5.68%);

IR(KBr)cm$^{-1}$: 1770(β-lactam), with narrow sharp peaks characteristic of the crystal being in evidence at 1670, 1190 and 1170.

EXAMPLE 5

In 25 ml of water was dissolved 5.5 g of a lyophilizate of 7β-[2-(2-imino-4-thiazolin-4-yl)acetamido]-3-[1-[2-(N,N-dimethylamino)ethyl]-1H-tetrazol-5-yl]thiomethyl-3-cephem-4-carboxylic acid obtained in Example 1-(2) (purity 93% on anhydrate basis), followed by the addition of 25 ml of acetone and, then, 4 ml of 12N-HCl. After an additional 100 ml of acetone was added, the mixture was stirred at 15° C. for 1 hour, after which time 50 ml of acetone was further added. The mixture was stirred for 1 hour and filtered. The solid product was washed 4 times with 10 ml portions of acetone. Upon drying, there was obtained 5.55 g crystals of said carboxylic acid dihydrochloride monohydrate.

(Yield: 92% on its pure product basis)

Elemental analysis, for $C_{18}H_{23}N_9O_4S_3.2HCl.H_2O$: Calcd.: C, 35.06; H, 4.41; N, 20.45; S, 15.60; Cl, 11.50; Found: C, 34.48; H, 4.48; N, 20.55; S, 15.22; Cl, 11.49

The powder X-ray diffraction pattern of this product showed that it was a crystalline powder, with its purity as determined by high-speed liquid chromatography being 99.4% on its anhydrate basis.

EXAMPLE 6

To 6.2 g of 7β-[2-(2-imino-4-thiazolin-4-yl)acetamido-3-[1-[2-(N,N-dimethylamino)ethyl]-1H-tetrazol-5-yl]thiomethyl-3-cephem-4-carboxylic acid dihydrochloride 1.5 hydrate obtained by the same manner as in Example 4-(I) was added 19 ml of 2N-HCl and the resultant solution was stirred at 5° C. together with 250 ml of ethanol for 2 hours. The mixture was further stirred at 10° C. for 2 hours, after which the precipitate was collected by filtration, washed 4 times with 15 ml portions of ethanol, dried in the air and, then, dried under reduced pressure and at 30° C. By the above procedure was obtained 5.6 g of said carboxylic acid dihydrochloride dihydrate.

By powder X-ray diffraction and polarizing microscopic determinations, this product was established to be crystalline.

EXAMPLE 7

(1) 5.0 l of an aqueous solution acidifed by 12N-HCl to pH 2.0 containing 510 g of 5β-[2-(2-imino-4-thiazolin-4-yl)acetamido]-3-[1-[2-(N,N-dimethylamino)ethyl]-1H-tetrazol-5-yl]thiomethyl-3-cephem-4-carboxylic acid obtained by repeating ten times in the same procedure as Example 1-(2) was cooled to 10° C. and, after addition of 7.0 g of activated charcoal, the solution was stirred for 5 minutes. The charcoal was removed by filtration and washed with 500 ml of water. The filtrate was combined with the washings and concentrated to 2.28 l under reduced pressure and at an interval temperature of 15° to 17° C. The concentrated solution was filtered again and washed. The filtrate and washing were 2.38 l, containing 478 g of said carboxylic acid. To the filtrate was added 0.2 l of acetone, followed by the addition of 170 ml of 12N-HCl. Then, 7 l of acetone was added over a period of 10 minutes. The solution was stirred at 5° to 10° C. for 2 hours, then an additional 7 l of acetone was added over 30 minutes, followed by stirring for an additional hour. The mixture was allowed to stand overnight and the resultant crystals were recovered by filtration and washed 4 times with 1 l portions of acetone. The crystals (A portion of the crystalline product was taken and dried in a desiccator at room temperature and at 30 mmHg for 30 minutes. The dried crystal contained 8.9% of water with 2.2% of acetone being incorporated. The calculated water content based on $C_{18}H_{23}N_9O_4S_3.2HCl.3H_2O$: 8.28%) were transferred to a separate glass filter and a nitrogen gas previously moistened by passage through a water-containing stripping bottle (the water temperature held at 25° to 30° C.) was passed through the bed of crystals at a flow rate of 8l/min. for 6 hours. The crystals (Water Content of a sample was 19.5%; calcd. Water Content based on $C_{18}H_{23}N_9O_4S_3.2HCl. 8H_2O$: 19.41%. This product contained no acetone, with its powder X-ray diffraction pattern attesting to crystallinity) were spread into a bed as thick as about 3 cm and dried at 30° C. and under a vacuum of 5 mmHg for 1.5 hours (Water Content of a sample was 17.2%; the calculated content based on $C_{18}H_{23}N_9O_4S_3.2HCl.7H_2O$: 17.4%). The crystals were further dried under the same conditions for 1.5 hours (Water Content was 15.4%, the calculated content based on $C_{18}H_{23}N_9O_4S_3.2HCl.6H_2O$ being 15.3%) and, then, for another 1.5 hours (After which time Water Content was 13.3%, with the calculated Water Content based on $C_{18}H_{23}N_9O_4S_3.2HCl.5H_2O$ being 13.08%). The crystals were further dried for 1.5 hours (Water Content became 10.5%, with the calculated Water Content based on $C_{18}H_{23}N_9O_4S_3.2HCl.4H_2O$ being 10.75%). After drying under the same conditions for another 1.5 hours, the crystals had the following properties.

Water content: 8.50% (calcd. Water Content based on $C_{18}H_{23}N_9O_4S_3.2HCl.3H_2O$: 8.28%); Powder X-ray diffraction pattern: crystalline; Cl content (determined by titration of $AgNO_3$): 10.6%(calcd. for $C_{18}H_{23}N_9O_4S_3.2HCl.3H_2O$: 10.8%)

(2) The crystals obtained in (1) above were dried at 30° C. and at 2 mmHg in the presence of phosphoric anhydride for 5 hours.

By this procedure was obtained 510 g of a crystaline product. Water Content: 5.7% (calcd. Water Content based on $C_{18}H_{23}N_9O_4S_3.2HCl.2H_2O$: 5.68%); Powder X-ray diffraction pattern: crystalline.

IR(KBr)cm$^{-1}$: 1770(β-lactam), with sharp peaks characteristic of crystals at 1670, 1190(sh.) and 1170.

(3) The crystals obtained in (2) above were dried at 30° C. and under a vacuum of 2 mmHg in the presence of phosphoric anhydride for 8 hours.

By this procedure was obtained 495 g of a crystalline product.

Water Content: 3.12% (calcd. for $C_{18}H_{23}N_9O_4S_3.2HCl.H_2O$: 2.92%); Purity as anhydrate(determined by high-speed liquid chromatography): 99.5%; Powder X-ray diffraction pattern: crystalline;

Elemental analysis, for $C_{18}H_{23}N_9O_4S_3.2HCl.H_2O$:
Calcd.: C, 35.06; H, 4.41; N, 20.45; S, 15.60; Cl, 11.50
Found: C, 34.78; H, 4.51; N, 20.62; S, 15.31; Cl, 11.77
$[a]_D^{20}$ (C=1%, $H_2O$)= +67.0°;

Residual solvent (acetone) — no more than 50 ppm; Cl content (determined by titration of $AgNO_3$): 11.4%, calcd. 11.50%; λmax ($H_2O$): 258 mμ (ε 19,500); Bioassay *: 865 mcg/ml.

*The bioassay by the cylinder method was carried out using 7β-[2-(2-imino-4-thiazolin-4-yl)acetamido]-3-[1-[2-(N,N-dimethylamino)ethyl]-1H-tetrazol-5-yl]thiomethyl-3-cephem-4-carboxylic acid .2H Cl salt as the standard product against *Bacillus subtilis* ATCC 6633 as the assay microorganism.

The potency of the anhydrous zwitter ion compound was 1000 mcg/ml. The calculated potency of a sample containing 2 moles of HCl per mole of the zwitter ion compound and none of non-bonding hydrochloric acid, water, residual solvent or other impurity is 878 mcg/ml.

EXAMPLE 8

In 20 ml of water was dissolved 5.26 g of a lyophilizate of 7β-[2-(2-imino-4-thiazolin-4-yl)acetamido]-3-[1-[2-(N,N-dimethylamino)ethyl]-1H-tetrazol-5-yl]thiomethyl-3-cephem-4-carboxylic acid obtained in Example 1-(2) (Water Content: 3.1%; the zwitter ion content as determined by high-speed liquid chromatography: 93.5%). To the solution was added 20 ml of acetone, followed by addition of 4 ml of 10N-HCl. Then, 96 ml of acetone was added with stirring at 20° C. over a period of 10 minutes. After the mixture was stirred for 2 hours, 72 ml of acetone was further added over a period of 20 minutes. After the addition had been completed, the mixture was stirred for 30 minutes and the resultant crystals were collected by filtration and washed 5 times with 15 ml portions of acetone. The crystals were dried in moisture-laden air (relative humidity 58%) for 2 hours. By this procedure were obtained 6.0 g of moist crystals, with its Water Content being 13%. This product was further dried under reduced pressure for 2 hours, whereupon 5.7 g of crystals (said carboxylic acid 2HCl.4H$_2$O) were obtained. Water Content: 10.9% (Calcd. for $C_{18}H_{23}N_9O_4S_3.2HCl.4H_2O$: 10.8%); Purity as anhydrate: (determined by high-speed liquid chromatography): 99.6%; Powder X-ray diffraction pattern: crystalline.

(2) In the presence of phosphoric anhydride, 3 g of the crystals obtained in (1) above were dried in a vacuum of 5 mmHg at 30° C. for 2 hours and at 50° C. for 5 hours. The procedure yielded 2.6 g powders of said carboxylic acid. 2HCl.0.1 H$_2$O.

Water Content: 0.3% (calcd. for $C_{18}H_{23}N_9O_4S_3 \cdot 2HCl \cdot 0.1H_2O$: 0.3%); Powder X-ray diffraction pattern: non-crystalline; polarizing microscopy: As the slide was rotated, interference colors were observed through crossed Nicol prisms, attesting to optical anisotropy and therefrom crystalline powders. Purity as anhydrate (determined by high-speed liquid chromatography): 99.6%.

EXAMPLE 9

(1) To 5 ml of an aqueous solution containing 7β-[2-(2-imino-4-thiazolin-4-yl)acetamido]-3-[1-[2-(N,N-dimethylamino)ethyl]-1H-tetrazol-5-yl]thiomethyl-3-cephem-4-carboxylic acid obtained in Example 1-(2) (As determined by high-speed liquid chromatography, this solution contained 1.05 g of the above carboxylic acid and 15 mg of 1-[2-(N,N-dimethylamino)ethyl]-5-mercapto-1H-tetrazole as well as traces of other impurities) was added 1.0 ml of 4N-HCl and the resultant solution was gradually added dropwise to 300 ml of acetone previously cooled to 5° C., with stirring. The powdery precipitate was collected by filtration, washed 4 times with 5 ml portions of acetone and dried under reduced pressure. By the above procedure was obtained 1.2 g of said carboxylic acid .2HCl. 1.2H₂O in powdery form.

Water Content: 3.45% (calcd. for $C_{18}H_{23}N_9O_4S_3 \cdot 2HCl \cdot 1.2H_2O$: 3.48%); Cl content (determined by titration of AgNO₃): 11.6% (calcd. for $C_{18}H_{23}N_9O_4S_3 \cdot 2HCl \cdot 1.2H_2O$: 11.4%); Purity as anhydrate (determined by high-speed liquid chromatography): 96.2% Powder X-ray diffraction pattern: non-crystalline.

(2) 0.3 g of the powder obtained in (1) above were spread in a dish and allowed to absorb moisture in a sealed vessel containing a saturated aqueous solution of NaBr at 25° C. overnight. The powders were moistened, then became oily and finally solidified. This solid was dried under reduced pressure to obtain 0.3 g of said carboxylic acid.2HCl.2.3H₂O in crystalline form. Water Content: 6.6% (calcd. for $C_{18}H_{23}N_9O_4S_3 \cdot 2HCl \cdot 2.3H_2O$: 6.5%); purity 95.2%; Cl content (determined by elemental analysis): 11.5% (calcd. 11.1%); Powder X-ray diffraction pattern: crystalline.

EXAMPLE 10

(1) To 1.1 l of dichloromethane was added 42.4 g of 7-amino-3-[1-[2-(N,N-dimethylamino)ethyl]-1H-tetrazol-5-yl]thiomethyl-3-cephem-4-carboxylic acid and, under stirring at −10° C., 59.8 g of dicyclohexylamine was added over a period of 5 minutes. After stirring for 20 minutes, 154 g of a solution of 4-chloro-3-oxo-butyryl chloride in dichloromethane (1.4 mol/kg) was added over a period of 35 minutes. After stirring for 35 minutes, 22 g of the same solution was further added, followed by stirring for 20 minutes. To this solution was added 300 ml of water together with 20 ml of 5N-HCl and the mixture was stirred at 25° C. for 30 minutes, then it was filtered and washed with water. The filtrate combined with washing was washed with dichloromethane and the dichloromethane layer was extracted with water. To the combined water layers was added 12.5 g of thiourea and the mixture was adjusted to pH 5.0 with sodium hydrogen carbonate and allowed to stand at room temperature for 3 hours. The mixture was further allowed to stand at 10° C. overnight and, then, adjusted to pH 5.2 with sodium hydrogen carbonate. This solution was passed through a column of Amberlite XAD-2(100–200 mesh; 2.5 l) which was rinsed with 7.5 l of water and eluted with 4 l of 15% methanol and, then, with 6 l of 40% methanol in 6 fractions. The 2nd to 6th fractions eluted with 40% methanol were combined, concentrated and lyophilized. The above procedure yielded 37.1 g of 7β-[2-(2-imino-4-thiazolin-4-yl)acetamido]-3-[1-[2-(N,N-dimethylamino)ethyl]-1H-tetrazol-5-yl]thiomethyl-3-cephem-4-carboxylic acid.

IR(KBr) cm⁻¹: 1765(β-lactam)

NMR(60MHz, D₂O) τ: 3.45(s, thiazoline 5-H), 4.35(Cl, 7-H), 4.88(d, 6-H), 5.0-6.7(m, 5×CH₂), 6.96(s, 2×CH₃);

Cl content (elemental analysis): no more than 0.1%; $N_a^+$ content (atomic absorption spectroscopy): no more than 100 ppm.

(2) A lyophilizate of 7β-[2-(2-imino-4-thiazolin-4-yl)acetamido]-3-[1-[2-(N,N-dimethylamino)ethyl]-1H-tetrazol-5-yl]thiomethyl-3-cephem-4-carboxylic acid as obtained in (1) above was treated in a similar manner as in (3) and (4) of Example 1 to obtain said carboxylic acid dihydrochloride 0.64 hydrate in powdery form.

NMR(60 MHz, D₂O) τ: 3.20(s, thiazoline 5-H), 4.25(d, 7-H), 4.75(d, 6-H), 4.9–6.5(m, 5 × CH₂), 6.85(s, 2 × CH₃)

EXAMPLE 11

While a mixture of 3 ml of 1.5N-HCl and 3 ml of n-propanol was stirred at 10° C., 0.53 g of 7β-[2-(2-imino-4-thiazoline-4-yl)acetamido]-3-[1-[2-(N,N-dimethylamino)ethyl]-1H-tetrazol-5-yl]thiomethyl-3-cephem-4-carboxylic acid obtained in Example 10-(1) was added. Then, following the addition of 9 ml of n-propanol, the mixture was stirred at 10° C. for 5 hours, then 9 ml of n-propanol was added. The mixture was allowed to stand at 5° C. overnight. The extracted crystals were collected by filtration, dried in the air and finally dehydrated to obtain 0.50 g of said carboxylic acid dihydrochloride dihydrate in crystalline form.

IR(KBr)cm⁻¹: 1770(β-lactam), 1670, 1190, 1170

Elemental analysis, for $C_{18}H_{23}N_9O_4S_3 \cdot 2HCl \cdot 2H_2O$: Calcd.: C, 34.07; H, 4.61; N, 19.86; Cl, 11.17; Found: C, 33.81; H, 4.50; N, 20.11; Cl, 10.98

TEST

One sample each of the following compounds was stored in a sealed vial at 50° C. for 4 weeks.

The sodium salt, zwitter ion, and monohydrochloride of 7β-[2-(2-imino-4-thiazoline-4-yl)acetamido]-3-[1-[2-(N,N-dimethylamino)ethyl]-1H-tetrazol-5-yl]thiomethyl-3-cephem-4-carboxylic acid, as well as the lyophilized powders of said acid dihydrochloride (amorphous powders, Example 4-(2)), the crystals of said acid dihydrochloride (Example 1-(3)) and the non-crystalline powders obtained by drying said dihydrochloride crystals (Example 1-(4)) as obtained in accordance with this invention.

The percent residue figures are as follows.

| Sample | Water Content | % Residue |
|---|---|---|
| Crystals of Example 1-(3) | 3.1 % | 99 % |
| Powders of Example 1-(4) | 1.9 | 98 |
| Product of Example 4-(2) | 0.50 | 86 |
| Sodium salt (lyophilizate) | 0.48 | 76 |
| Zwitter ion(lyophilizate) | 0.50 | 54 |
| Monohydrochloride (lyophilizate) | 0.58 | 73 |

EXAMPLE 12

2.49 g. of 7β-[2-(2-imino-4thiazolin-4-yl)acetamido]-3-[1-[2-(N,N-dimethylamino)ethyl]-1H-tetrazol-5-yl]thiomethyl-3-cephem-4-carboxylic acid obtained by the same procedure as in (1) of Example 10 was dissolved in 10 ml of 2N-HCl, followed by the addition of 25 ml of tetrahydrofuran. After standing overnight at 5°–10 C., the resulting crystals were filtered and washed with tetrahydrofuran. Drying of the crystals in vacuo for 2.5 hours afforded 2.4 g of the crystals of said carboxylic acid. 2HCl.6H$_2$O.

Water Content: 15.1%, Powder X-ray diffraction pattern: crystalline.

EXAMPLE 13

2.0 g of 7β-[2-(2-imino-4-thiazolin-4-yl)acetamido]-3-[1-[2-(N,N-dimethylamino)ethyl]-1H-tetrazol-5-yl]thiomethyl-3-cephem-4-carboxylic acid obtained by the same procedure as in (1) of Example 10 was dissolved in 13 ml of a 30% aqueous sodium chloride solution at 25° C. After the addition of 7 ml of 2N-HCl, the solution was stirred for 4 hours at 20° C. The resulting precipitates were collected by filtration and washed with a cold 10% aqueous sodium chloride solution. After 2 day's storage in a desiccator the relative humidity in which was controlled at 58% by an aqueous solution saturated with sodium bromide dihydrate, 1.8 g of said carboxylic acid. 2HCl.5H$_2$O were obtained in crystalline form.

Water Content: 12.9%, Powder X-ray diffraction pattern: crystalline

EXAMPLE 14

To the mixture of 12.5 g. of 7β-amino-3-[1-[2-(N,N-dimethylamino)ethyl]-1H-tetrazol-5-yl]thiomethyl-3-cephem-4-carboxylic acid and 180 ml of dichloromethane was added 11.6 g. of di-n-butylamine under stirring at −10° to −15° C. After 15 min. the clear solution was obtained. To this solution was added 39.0 ml of 4-chloro-3-oxo-butyryl chloride in dichloromethane (1.54 mM/ml) at −15° to −20° C. during 5 min. under stirring. After stirring for 15 min. at −10° C., 7β-(4-chloro-3-oxobutyramido)-3-[1-[2-(N,N-dimethylamino)ethyl]-1H-tetrazol-5-yl]thiomethyl-3-cephem-4-carboxylic acid hydrochloride was extracted with 40 ml and 25 ml portions of 1N-HCl from the reaction mixture. The extracted water layers were combined and washed twice with 30 ml portion each of dichloromethane. 5.7 g. of thiourea and 455 ml of acetone were added to the water layer and the mixture was stirred for 7 hours at 20° to 22° C. and left standing overnight. Filtration and washing with 4 portions of 60 ml. of acetone and drying in vacuo afforded 17.5 g. of the crystals of 7β-[2-(2-imino-4-thiazolin-4-yl)acetamido]-3-[1-[2-(N,N-dimethylamino)ethyl]-1H-tetrazol-5-yl]thiomethyl-3-cephem-4-carboxylic acid .2HCl.4H$_2$O. The acetone content of this crystals was shown by NMR spectrum to be 0.25 mole per 1 mole of said carboxylic acid.

NMR(60MHz, D$_2$O) τ: 3.20(s, thiazolin 5-H), 4.25(4, 7-H), 4.75(d, 6H-), 4.9–6.5(m, 5×CH$_2$), 6.85(s, 2×CH$_3$), 7.70(s, CH$_3$ of acetone)

Water Content: 10.5%, Powder X-ray diffraction pattern: crystalline.

EXAMPLE 15

To 1.0 g. of 7β-[2-(2-iminothiazolin-4-yl)acetamido]-3-[1-[2-(N,N-dimethylamino)ethyl]-1H-tetrazol-5-yl]thiomethyl-3-cephem-4-carboxylic acid obtained by the same procedure as in (1) of Example 10 was added 46 ml of water and 4 ml of 1N-HCl. After addition of 500 ml of acetone, the mixture was stirred for 2 hours and another 700 ml. of acetone was added, followed by left standing overnight at 5° C. The precipitated needles were collected by filtration, washed with acetone and dried in a desiccator for 15 hours at 15°–20° C. in vacuo, which afforded 0.4 g. of crystals.

Elemental analysis, for C$_{18}$H$_{23}$N$_9$O$_4$S$_3$.2HCl.-H$_2$O.0.13 acetone: Calcd.: C, 35.39; H, 4.49: N, 20.20; S, 15.38; Found: C, 34.78; H, 4.53; N, 19.87; S, 15.38

Water Content: 2.91%, Powder X-ray diffraction pattern: crystalline.

EXAMPLE 16

To 1.7 g. of 7β-[2-(2-imino-4-thiazolin-4-yl)acetamido]-3-[1-[2-(N,N-dimethylamino)ethyl]-1H-tetrazol-5-yl]thiomethyl-3-cephem-4-carboxylic acid was added 8 ml. of 2N-HCl, followed by addition of 73 ml. of ethanol. After left standing overnight at 5° C., the precipitated crystals were collected by filtration and dried for 30 min. in vacuo, which afforded 1.0 g. of crystals. Ethanol content of this crystals was shown by NMR(60 MHz, D$_2$O) spectrum to be 0.65 mole per 1 mole of said carboxylic acid. Water Content: 7.70%; Calcd. for C$_{18}$H$_{23}$N$_9$O$_4$S$_3$.2HCl.3H$_2$O. 0.65 ethanol: 7.92%; Powder X-ray diffraction pattern: crystalline.

EXAMPLE 17

To 1.64 g. of 7β-[2-(2-imino-4-thiazolin-4-yl)acetamido]-3-[1-[2-(N,N-dimethylamino)ethyl]-1H-tetrazol-5-yl]thiomethyl-3-cephem-4-carboxylic acid obtained by the same procedure (1) of Example 10 were added 10 ml of anhydrous methanol and 6.2 ml of 1N-methanolic HCl (anhydrous). The mixture was stirred to obtain a clear solution, which was added to 150 ml. of anhydrous diethylether under stirring. The resulting precipitates were filtered, washed with anhydrous diethylether and dried in vacuo to afford 1.74 g. of the powder of said carboxylic acid .2HCl.

NMR(60 MHz, D$_2$O) τ: 3.20(s, thiazolin 5-H), 4.25(d, 7-H), 4.75 (d, 6-H), 4.9–6.5(m, 5×CH$_2$), 6.85(s, 2×CH$_3$)

Elemental analysis, for C$_{18}$H$_{23}$N$_9$O$_4$S$_3$.2HCl: Calcd.: C, 36.12; H, 4.21; N, 21.06; Found: C, 36.20; H, 4.25; N, 20.80

Powder X-ray diffraction pattern: amorphous
Polarizing microscopic observation: amorphous

What we claim is:

1. A crystalline cephalosporin derivative having the formula;

[Chemical structure: 7β-[2-(2-imino-4-thiazolin-4-yl)acetamido]-3-[1-[2-(N,N-dimethylamino)ethyl]-1H-tetrazol-5-yl]thiomethyl-3-cephem-4-carboxylic acid . 2HCl . nH$_2$O]

where n is a number from 0.1 to 4.

2. A solid cephalosporin derivative as claimed in claim 1, wherein n is a number from 1 to 2.

3. A solid cephalosporin derivative as claimed in claim 1, wherein n is 1.

4. A solid cephalosporin derivative as claimed in claim 1, wherein n is 2.